(12) United States Patent
Ozeki et al.

(10) Patent No.: US 9,103,726 B2
(45) Date of Patent: Aug. 11, 2015

(54) STIMULATED RAMAN SCATTERING DETECTION APPARATUS

(75) Inventors: Yasuyuki Ozeki, Kawasaki (JP); Kazuyoshi Itoh, Kawanishi (JP); Keisuke Nose, Tokyo (JP)

(73) Assignee: CANON KABUSHIKI KAISHA (JP)

(*) Notice: Subject to any disclaimer, the term of this patent is extended or adjusted under 35 U.S.C. 154(b) by 106 days.

(21) Appl. No.: 14/002,143

(22) PCT Filed: Mar. 2, 2012

(86) PCT No.: PCT/JP2012/056041
§ 371 (c)(1),
(2), (4) Date: Oct. 10, 2013

(87) PCT Pub. No.: WO2012/121357
PCT Pub. Date: Sep. 13, 2012

(65) Prior Publication Data
US 2014/0043606 A1    Feb. 13, 2014

(30) Foreign Application Priority Data
Mar. 4, 2011 (JP) ................. 2011-048110

(51) Int. Cl.
*G01J 3/44* (2006.01)
*G01N 21/65* (2006.01)
(Continued)

(52) U.S. Cl.
CPC ............. *G01J 3/4412* (2013.01); *G01J 3/433* (2013.01); *G01J 3/44* (2013.01); *G01N 21/65* (2013.01); *G01N 2021/655* (2013.01); *H01S 3/005* (2013.01); *H01S 3/2391* (2013.01)

(58) Field of Classification Search
CPC ............ G01N 2021/655; G01N 21/65; G01N 2021/653; H01S 3/005–3/0092; G01J 3/4412; G01J 3/44
See application file for complete search history.

(56) References Cited

U.S. PATENT DOCUMENTS 5,777,736 A * 7/1998 Horton ............... 356/456
5,822,471 A * 10/1998 McGinnis ............ 385/1
(Continued)

FOREIGN PATENT DOCUMENTS

EP   0 869 589 A2   10/1998
EP   2 439 516 A1    4/2012
(Continued)

OTHER PUBLICATIONS

Extended European Search Report issued in Counterpart European Patent Application No. 12754785.9, dated Jul. 25, 2014.
(Continued)

*Primary Examiner* — Michael A Lyons
*Assistant Examiner* — Shawn Decenzo
(74) *Attorney, Agent, or Firm* — Rossi, Kimms & McDowell LLP

(57) ABSTRACT

The stimulated Raman scattering detection apparatus includes first and second light pulse generators (1, 2) respectively generating first and second light pulses with first and second pulse periods, an optical system combining the first and second light pulses and focusing the combined light pulses onto a sample, and a detector (10) detecting the second light pulses intensity-modulated by stimulated Raman scattering generated by focusing of the combined light pulses onto the sample. The second light pulse generator divides each raw light pulse emitted with the second pulse period into two light pulses, delays one of the two light pulse with respect to the other thereof and combines the one light pulse divided from one raw light pulse and delayed, with the other light pulse divided from another raw light pulse emitted after the one raw light pulse, to generate the second light pulse.

6 Claims, 6 Drawing Sheets

(51) Int. Cl.
*G01J 3/433* (2006.01)
*H01S 3/00* (2006.01)
*H01S 3/23* (2006.01)

(56) References Cited

U.S. PATENT DOCUMENTS

2014/0268111 A1* 9/2014 Couch et al. .............. 356/73.1
2014/0268131 A1* 9/2014 Tamada .................... 356/301

FOREIGN PATENT DOCUMENTS

JP  2007-278768 A  10/2007
WO  2010/140614 A1  12/2010

OTHER PUBLICATIONS

Csornyei et al. "All-optical intensity noise suppression for solid-state and semiconductor lasers" Journal of Telecommunications and Information Technology, Feb. 2005, pp. 65-70.

Xue et al. "Analysis and Evaluation of Phase Noise Suppression by Incoherent Addition for a Passive Mode-Locked Fiber Laser" IQEC/CLEO Pacific Rim 2011, Aug. 28-Sep. 1, 2011, pp. 1148-1150, Sydney, Australia.

Tsuchida "Pulse-Timing Noise Reduction of a Mode-Locked Laser Diode by Incoherent Addition", IEEE Journal of Selected Topics in Quantum Electronics, vol. 9, No. 4, Jul./Aug. 2003, pp. 1081-1092.

Dake, et al., "Principle Confirmation of Stimulated Raman Scattering Microscopy", Optics & Photonics Japan, 2008, 5pC12.

Freudiger, et al., "Label-Free Biomedical Imaging With High Sensitivity by Stimulated Raman Scattering Microscopy", Science, vol. 322, Dec. 9, 2008, pp. 1857-1861.

International Search Report issued May 22, 2012 for PCT/JP2012/056041.

* cited by examiner (1) $\tau_s/2 - \tau_s/6 \leq T \leq \tau_s/2 + \tau_s/6$
(2) $|\Delta L - c\tau_s/2| \leq c\tau_s/6$ FIG. 3A $L_0$ 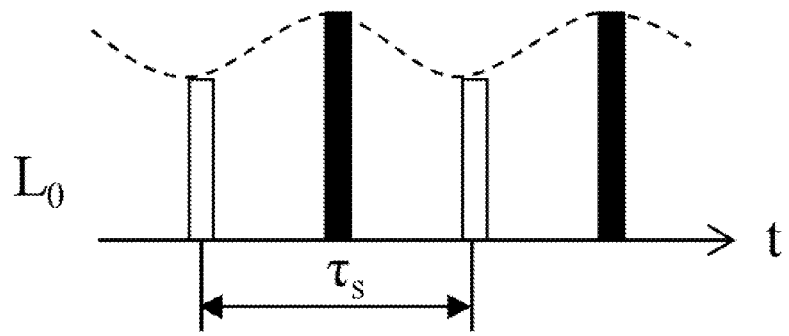
FIG. 3B $L_1$
FIG. 3C $L_2$ 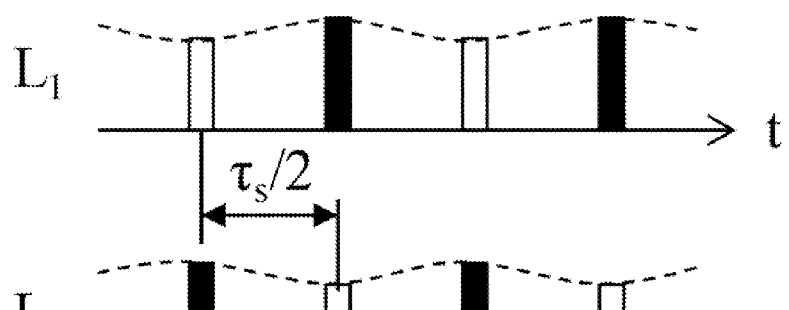
FIG. 3D $L_{12}$ 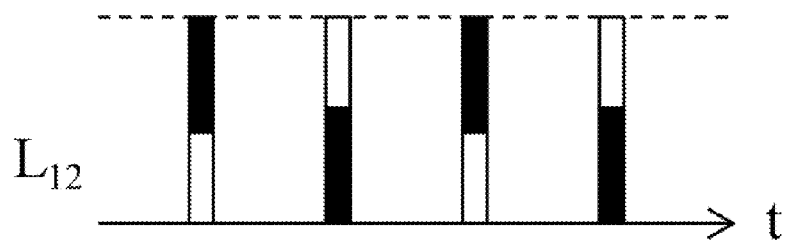

(1) $\tau_s/2 - \tau_s/6 \leq T \leq \tau_s/2 + \tau_s/6$ AND (3) $|T - (\tau_s/2)| \geq 2p$
(2) $|\Delta L - c\tau_s/2| \leq c\tau_s/6$ AND (4) $|\Delta L - c\tau_s/2| \geq 2cp$

STIMULATED RAMAN SCATTERING DETECTION APPARATUS

This application is a U.S. National Phase Application of PCT International Application PCT/JP2012/056041 filed on Mar. 2, 2012 which is based on and claims priority from JP 2011-048110 filed on Mar. 4, 2011 the contents of which is incorporated in its entirety by reference.

TECHNICAL FIELD

The present invention relates to a stimulated Raman scattering detection apparatus to be used for a microscope, an endoscope and the like performing molecular vibration imaging by utilizing stimulated Raman scattering.

BACKGROUND ART

A stimulated Raman scattering (SRS) detection apparatus that is one of detection apparatuses utilizing a Raman scattering principle has been proposed in "Principle confirmation of stimulated Raman scattering microscopy" by Fumihiro Dake et al. and "Label-free biomedical imaging with high sensitivity by stimulated Raman scattering microscopy" by Chiristian W. Freudiger et al. The principle of the SRS detection apparatus is as follows.

When two light pulses whose light frequencies are mutually different are focused onto a sample, a coincidence of a difference between the light frequencies of the two light pulses with a molecular vibration frequency causes a phenomenon of stimulated Raman scattering at a light-focused point, the stimulated Raman scattering modulating intensity of the light pulse. Detection of an intensity-modulated light component (detection light) from the light pulse intensity-modulated by the stimulated Raman scattering and emerged from the sample enables molecular vibration imaging in which vibration information of molecules of the sample is reflected.

However, the SRS detection apparatus requires a light source generating extremely low noise close to a shot noise limit, which provides a restriction to a laser light source. Thus, the SRS detection apparatus needs a light source using a solid laser or an optical parametric oscillator which requires frequent extensive maintenance.

On the other hand, a stable small laser source such as a fiber laser generates a large intensity noise component in its laser output because the laser output is small. Thus, deterioration of an S/N (signal-to-noise) ratio of the laser source due to an influence of the intensity noise component becomes a problem when such a small laser source is used for the SRS detection apparatus.

SUMMARY OF INVENTION

The present invention provides an SRS detection apparatus capable of reducing the intensity noise component included in the light pulses to be focused onto the sample to improve the S/N ratio of the detection light. The present invention provides as an aspect thereof a stimulated Raman scattering detection apparatus including a first light pulse generator configured to generate first light pulses with a first pulse period, a second light pulse generator configured to generate second light pulses with a second pulse period shorter than the first pulse period, the second light pulse having a light frequency different from that of the first light pulse, an optical system configured to combine the first and second light pulses and configured to focus the combined first and second light pulses onto a sample, and a detector configured to detect the second light pulses intensity-modulated by stimulated Raman scattering generated by focusing of the combined first and second light pulses onto the sample. The second light pulse generator includes a divider configured to divide each of raw light pulses into two light pulses, the raw light pulses being emitted from a light source with the second pulse period, a delayer configured to delay one of the two light pulses with respect to the other thereof, and a combiner configured to combine the one light pulse divided from one of the raw light pulses and delayed by the delayer, with the other light pulse divided from another one of the raw light pulses emitted from the light source after the one raw light pulse, to generate the second light pulse. Further features and aspects of the present invention will become apparent from the following description of exemplary embodiments with reference to the attached drawings.

BRIEF DESCRIPTION OF DRAWINGS

FIGS. 3A to 3D show processes performed on light pulse trains by the delaying and combining part shown in FIG. 2.

DESCRIPTION OF EMBODIMENTS

Embodiments of the present invention will hereinafter be described with reference to the attached drawings.

Example 1

Figure 1:
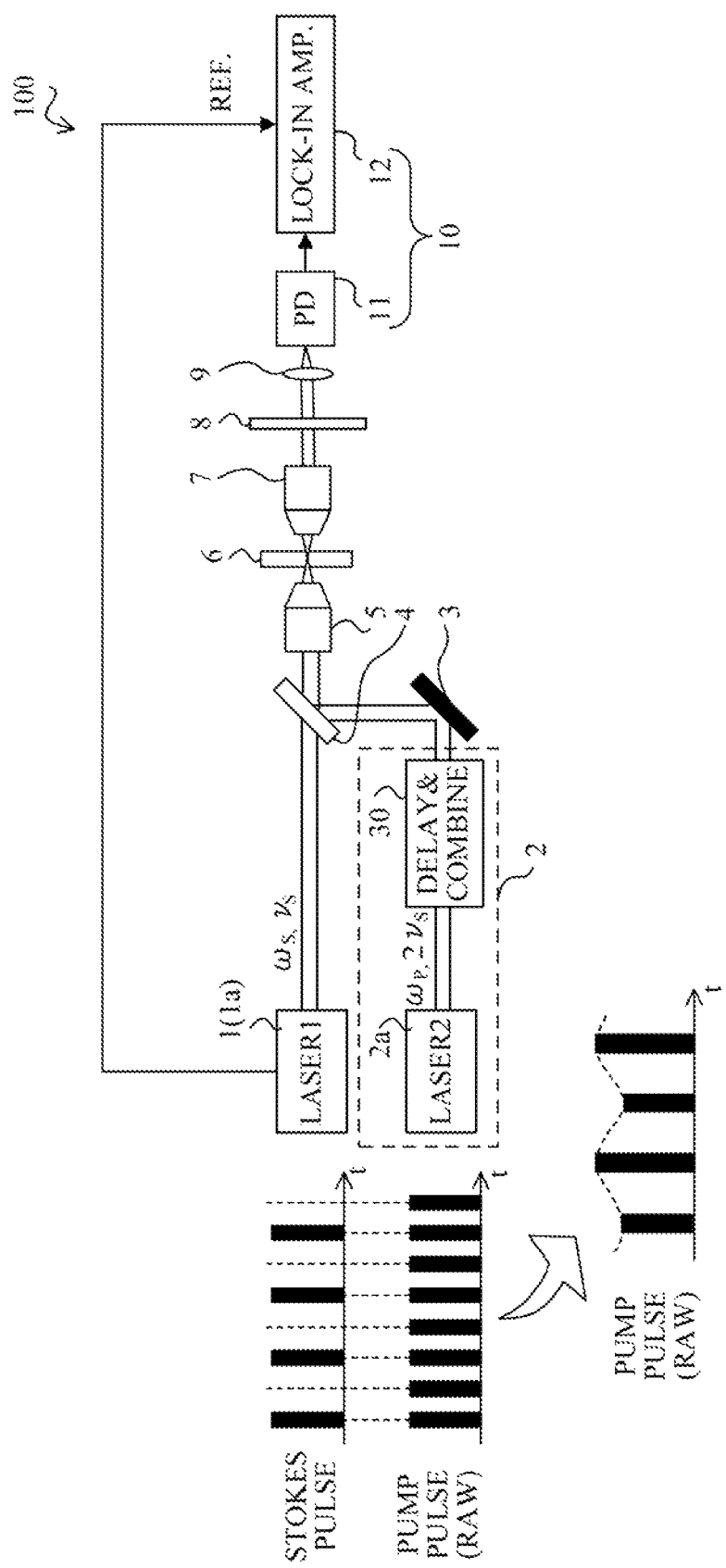
FIG. 1 is a block diagram showing a configuration of a stimulated Raman scattering (SRS) detection apparatus that is Embodiment 1 of the present invention.

FIG. 1 schematically shows a configuration of a stimulated Raman scattering (SRS) detection apparatus that is a first embodiment (Embodiment 1) of the present invention. The SRS detection apparatus 100 can be used as apparatuses such as a microscope and an endoscope for observation, measurement, diagnosis and other usages.

The SRS detection apparatus 100 of this embodiment includes a first light pulse generator 1 that generates a first light pulse train to be used as Stokes light, and a second light pulse generator 2 that generates a second light pulse train to be used as pump light. Moreover, the detection apparatus 100 includes an optical system by a mirror 3, a half mirror 4, a first objective lens 5, a second objective lens 7, a color filter 8 and a collective lens 9. Furthermore, the detection apparatus 100 includes a detector 10 constituted by a photodiode 11 that is a light-receiving element and a lock-in amplifier 12 that is an electronic circuit synchronously detecting output signals of the photodiode 11.

A sample 6 that is an object to be measured is placed between the first objective lens 5 and the second objective lens 7.

The first light pulse generator 1 is constituted by a first light source 1a that repeatedly emits first light pulses forming the first pulse train with a first pulse period. A fiber laser light source is, for example, used as the first light source 1a. The first light pulse train has, for example, a first light frequency of $\omega_S$ that corresponds to a wavelength of 1000 nm, a first pulse width of 1-10 ps (picoseconds) that is desirable to obtain a high discrimination ability for molecular vibration and a first repetition frequency of 55 MHz that corresponds to a first pulse period of 18.2 ns. The first light pulse train (Stokes Pulse) is generated as shown in an area further left than the first light pulse generator 1 in FIG. 1 where t represents time.

The second light pulse generator 2 is constituted by a second light source 2a that repeatedly emits (oscillates), with a second pulse period, raw light pulses to be used to generate second light pulses forming the second pulse train. The second light pulse generator 2 further includes a delaying and combining part 30 that generates the second light pulses (second light pulse train) from the raw light pulses (raw light pulse train). A fiber laser light source is, for example, used as the second light source 2a as well as the first light source 1a. The second light pulse train has, for example, a second light frequency of $\omega_P$ that is adjustable up to a frequency corresponding to a wavelength of 770 nm, a second pulse width that is substantially equal to the first pulse width and a second repetition frequency of 110 MHz that corresponds to a second pulse period of 9.1 ns. The second light frequency of the second light pulse train is adjusted such that a frequency difference thereof from the first light frequency of the first light pulse train may coincide with a molecular vibration frequency of molecules to be measured in the sample 6. The raw light pulse train is generated as shown in an area further left than the second light pulse generator 2 in FIG. 1.

The delaying and combining part 30 performs processes of division, delaying and combination on each of the raw light pulses from the second light source 2a to generate the second light pulses forming the second light pulse train with the second pulse period. A detailed configuration of the delaying and combining part 30 will be described later.

In this embodiment, the repetition frequency (first repetition frequency) of the first light pulse train generated by the first light pulse generator 1 is set to ½ of the repetition frequency (second repetition frequency) of the second light pulse train generated by the second light pulse generator 2. In other words, the pulse period (second pulse period) of the second light pulse train is set to ½ of the pulse period (first pulse period) of the first light pulse train. In this embodiment, hereinafter, the repetition frequency of the first light pulse train is represented by $\nu_S$, and the repetition frequency of the second light pulse train is represented by $2\nu_S$. The pulse period (first pulse period) of the first light pulse train is represented by $\tau_S$, and the pulse period (second pulse period) of the second light pulse train is represented by $\tau_S/2$.

The above-described setting of the repetition frequencies (and the pulse periods) causes one first light pulse to be generated synchronously with a timing of generation of two second light pulses. The second pulse period may be one even number of the first pulse period is. Such generation of the first and second light pulses makes it possible to increase the number of times at which a stimulated Raman scattering effect is caused, as compared with a case of setting the repetition frequency of the first light pulse train to ⅓ or ⅕ of that of the second light pulse train, which enables acquisition of a molecular vibration image of the sample 6 with higher accuracy.

Although this embodiment uses the fiber laser light source as the first and second light sources 1a and 2a, other laser light sources than the fiber laser light source, such as a titanium-sapphire laser light source, may be used.

Moreover, this embodiment uses the separate light sources 1a and 2a for the first light pulse generator 1 and the second light pulse generator 2 and electrically connects both the light sources 1a and 2a with each other to synchronize them. However, while a laser light source is used as one of two light pulse generators, an optical parametric oscillator or the like which generates laser light having another repetition frequency may be used as the other of the two light pulse generators.

Furthermore, this embodiment describes a case of using the first light pulse train whose repetition frequency is lower than that of the second light pulse train as Stokes light and of using the second light pulse train as pump light. However, the first light pulse train whose repetition frequency is lower than that of the second light pulse train may be used as the pump light, and the second light pulse train may be used as the Stokes light. That is, the first light frequency $\omega_S$ and the second light frequency $\omega_P$ may be interchanged therebetween.

The second light pulse train whose repetition frequency is $2\nu_S$ and which is generated by the second light pulse generator 2 is subjected to directional change by the mirror 3 to enter the half mirror 4. Then, the second light pulse train is combined (or synthesized) on a same axis, at the half mirror 4, with the first light pulse train whose repetition frequency is $\nu_S$ and which is generated by the first light pulse generator 1. The combined light pulse train is focused (projected) onto the sample 6 through the first objective lens 5. This embodiment uses, as the first objective lens 5, a lens whose magnification is 40 and numerical aperture (NA) is 0.6.

In the light pulse train focused onto the sample 6, both of the first and second light pulses whose respective repetition frequencies are $\nu_S$ and $2\nu_S$ as mentioned above and only the second light pulse alternately appear every $1/(2\nu_S)$. Focusing of both of the first and second light pulses onto the sample 6 in a state where a frequency difference $(\omega_P-\omega_S)$ between the first and second light frequencies coincides with the molecular vibration frequency of the molecules to be measured in the sample 6 (every $1/\nu_S$) causes the stimulated Raman scattering. Thus, the stimulated Raman scattering causes intensity modulation of the second light pulse train with a frequency of $\nu_S$.

The first light pulses and the second light pulses intensity-modulated by the stimulated Raman scattering are emerged from the sample 6 and collimated by the second objective lens 7. This embodiment uses, as the second objective lens 7, a lens whose magnification is 40 and numerical aperture (NA) is 0.6, as well as the first objective lens 5. The first and second light pulses collimated by the second objective lens 7 enter the color filter 8 through which only the second light pulses are transmitted, and the second light pulses are collected by the collective lens 9.

The second light pulse train (second light pulses) collected by the collective lens 9 is photoelectrically converted by the photodiode 11 into an electrical signal that is output therefrom. The output signal from the photodiode 11 is input to the lock-in amplifier 12 to be synchronously detected with a lock-in frequency $\nu_S$ (that is, with the first pulse period $\tau_S$) corresponding to a frequency reference signal REF from the first light pulse generator 1. This synchronous detection makes it possible to detect only light that is an intensity-modulated component of the second light pulse train generated by the stimulated Raman scattering. Scanning the sample 6 by using such a detection method enables acquisition of the molecular vibration image of the molecules to be measured in the sample 6.

In the SRS detection apparatus 100 thus configured, the second light pulse train emitted from the fiber laser light source that is the second light source 2a includes intensity fluctuation due to intensity noise of the laser light source, as shown by an expanded view in FIG. 1. Direct focusing of the second light pulse train including such an intensity noise component onto the sample 6 causes deterioration of an S/N ratio of the light (detection light) detected by the lock-in amplifier 12. In other words, in order to improve the S/N ratio of the detection light, it is desirable to remove as much as possible the intensity noise component due to the second light source 2a from the second light pulse train to be focused onto the sample 6. Therefore, this embodiment provides the delaying and combining part 30 to the second light pulse generator 2.

Figure 2:
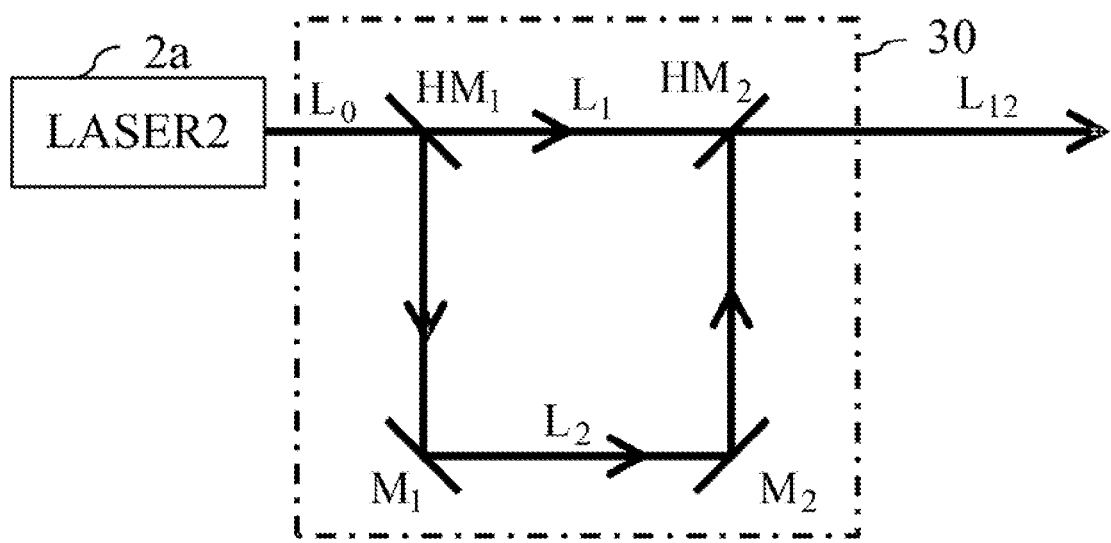
FIG. 2 is a block diagram showing a configuration of a delaying and combining part in the SRS detection apparatus of Embodiment 1.

FIG. 2 shows the detailed configuration of the delaying and combining part 30 in this embodiment. Moreover, FIGS. 3A to 3D show the raw light pulse emitted from the second light source 2a and processes performed thereon by the delaying and combining part 30.

In FIG. 2, the raw light pulse $L_0$ emitted from the second light source 2a enters a first half mirror (divider) $HM_1$ provided in the delaying and combining part 30 to be divided into a light pulse $L_1$ transmitted therethrough and a light pulse $L_2$ reflected thereby. Of these light pulses $L_1$ and $L_2$, the light pulse $L_2$ proceeds to a delaying optical path including mirrors $M_1$ and $M_2$, and the light pulse $L_1$ proceeds directly to a second half mirror (combiner) $HM_2$.

FIG. 3A shows the raw light pulses $L_0$ repeatedly emitted from the second light source 2a with the second pulse period, and FIG. 3B shows the light pulses $L_1$ transmitted through the first half mirror $HM_1$. The raw light pulses $L_0$ include the intensity noise (intensity fluctuation) component shown also in FIG. 1. The above-mentioned first pulse period $\tau_S$ corresponds to a pulse interval of the first light pulse train that is the Stokes light, and the raw light pulses $L_0$ are emitted from the second light source 2a with a pulse interval (second pulse period) of $\tau_S/2$ that is half of the pulse interval $\tau_S$.

Each of FIGS. 3A and 3B shows, with time t, the raw light pulses $L_0$ repeatedly emitted and the light pulses $L_1$ divided therefrom with alternate black and white bars.

The delaying optical path where the light pulse $L_2$ passes is an optical path starting from the first half mirror $HM_1$, via the mirrors $M_1$ and $M_2$, and reaching the second half mirror $HM_2$. An optical path length of this delaying optical path has an optical path length difference $\Delta L$ from an optical path from the first half mirror $HM_1$ to the second half mirror $HM_2$ where the light pulse $L_1$ passes. This optical path length difference $\Delta L$ is set so as to delay the light pulse $L_2$ with respect to the light pulse $L_1$ by a delay time T within a range shown by the following expression (1). That is, the delay time T is set so as to satisfy a condition shown by the expression (1).

$$\tau_S/2 - \tau_S/6 \le T \le \tau_S/2 + \tau_S/6 \quad (1)$$

Moreover, on the basis of the expression (1), the optical path length difference $\Delta L$ is set so as to have a relationship shown by the following expression (2) with the first pulse period $\tau_S$ and a light speed c. That is, the optical path length difference $\Delta L$ is set so as to satisfy a condition shown by the expression (2).

$$|\Delta L - c\tau_S/2| \le c\tau_S/6 \quad (2)$$

The expression (1) includes a case where the delay time T is equal to $\tau_S/2$. The meaning of $\pm\tau_S/6$ in the expression (1) will be described later. FIG. 3C show the light pulses $L_2$ delayed with respect to the light pulses $L_1$ by the delay time $T(=\tau_S/2)$. In FIG. 3C, at a same time as the light pulse $L_1$ shown by the white bar in FIG. 3B appears, the light pulse $L_2$, which is shown by the black bar and divided from the raw light pulse $L_0$ emitted one pulse period ($\tau_S/2$) before that light pulse $L_1$, appears. Similarly, at a same time as the light pulse $L_1$ shown by the black bar in FIG. 3B appears, the light pulse $L_2$, which is shown by the white bar and divided from the raw light pulse emitted one pulse period ($\tau_S/2$) before that light pulse $L_1$, appears. The raw light pulse $L_0$ emitted one pulse period ($\tau_S/2$) before is hereinafter referred to as a "previous raw light pulse".

When the delay time T is shifted with respect to $\tau_S/2$ by a time between $-\tau_S/6$ and $+\tau_S/6$, the light pulses $L_1$ and $L_2$ appear at a time shifted from "the same time". This applies to the following description.

The light pulse $L_2$ thus delayed and entering the second half mirror $HM_2$ is combined with the light pulse $L_1$ simultaneously entering the second half mirror $HM_2$. In other words, the delaying and combining part 30 combines the light pulse $L_2$ that is one of two light pulses divided from one raw light pulse $L_0$ and delayed, with the light pulse $L_1$ that is the other of two light pulses divided from another raw light pulse $L_0$ emitted from the second light source 2a after the one raw light pulse $L_0$. Such combination generates a second light pulse $L_{12}$ having intensity (hereinafter referred to as "combined intensity") corresponding to a sum of intensity of the light pulse $L_1$ divided from the raw light pulse $L_0$ without delay and intensity of the light pulse $L_2$ divided from the previous raw light pulse $L_0$ and delayed by the delay time T. The second light pulse $L_{12}$ thus generated proceeds from the delaying and combining part 30 toward the mirror 3 shown in FIG. 1.

Of the above-mentioned intensity noise included in the raw light pulse $L_0$, an intensity noise component generated with the first pulse period $\tau_S$ that is a generation period of the stimulated Raman scattering with which the first and second light pulses are simultaneously focused onto the sample 6 influences the S/N ratio in the lock-in amplifier 12. For example, when amplitude of this intensity noise component is constant, increase and decrease by a constant amount alternately appear in the intensity of the raw light pulse $L_0$ generated every second pulse period $\tau_S/2$ corresponding to half of the period of the intensity noise component, as shown in FIG. 3A.

Therefore, as shown in FIGS. 3B and 3C, increase and decrease of the intensity of the light pulse $L_1$ and increase and decrease of the intensity of the light pulse $L_2$ (divided from the previous raw light pulse $L_0$) to be combined with the light pulse $L_1$ are respectively alternated in an opposite relationship, and this relationship is alternated every second pulse period $\tau_S/2$. Accordingly, the combined intensity of the second light pulse $L_{12}$ generated by combining the light pulses $L_1$ and $L_2$ hardly changes every second pulse period $\tau_S/2$ (in other words, every first pulse period $\tau_S$) as shown in FIG. 3D, which makes the combined intensity of the second light pulse train approximately constant.

Thus, the delaying and combining part 30 can generate the second light pulse train including almost no intensity noise component that influences the S/N ratio in the lock-in amplifier 12.

Although this embodiment describes the case of setting the second pulse period to ½ of the first pulse period $\tau_S$, it is only necessary to set the second pulse period to a period shorter than the first pulse period $\tau_S$. That is, it is only necessary to be able to detect the second light pulse intensity-modulated by the stimulated Raman scattering, by matching detection timing with combination timing of the first light pulse train and the second light pulse train generated by the delaying and combining part 30.

Figure 4:
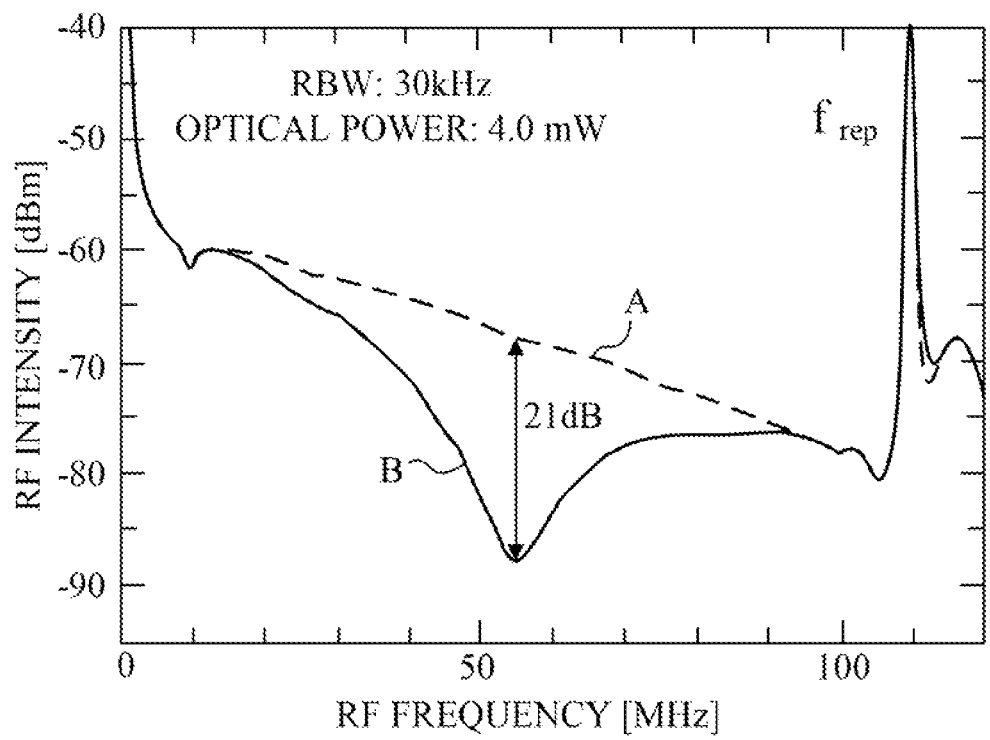
FIG. 4 shows an experiment result in Embodiment 1.

FIG. 4 shows a result of an actual experimental example based on this embodiment. In this experimental example, the second light pulse train has a repetition frequency of 109 MHz, a pulse width of 160 fs (femto seconds) and an intensity of 4 mW. In FIG. 4, a graph A shows the intensity noise included in the raw light pulse train before entering the delaying and combining part 30, and a graph B shows the intensity noise included in the second light pulse train generated through the delaying and combining part 30.

As shown by the graph B, generating the second light pulse train through the delaying and combining part 30 enabled reduction of the intensity noise component by 21 dB from the raw light pulse train at 55 MHz corresponding to the repetition frequency of the first light pulse train.

Next, description will be made of the meaning of the range of the delay time T shown by the expression (1) with reference to FIG. 5. The intensity of the raw light pulse train ($L_0$) emitted from the second light source 2a is expressed by $I_0(t)$ that is a function of time, and the intensities of the two divided light pulses ($L_1$ and $L_2$) are respectively expressed by $I_1(t)$ and $I_2(t)$. In addition, the combined intensity of the second light pulse train ($L_{12}$) that is the pump light is expressed by $I_{12}(t)$.

When $I_2$ is delayed from $I_1$ by the delay time T, the following expressions are established:

$$I_1(t) = I_0(t)/2$$

$$I_2(t) = I_0(t-T)/2$$

$$I_{12}(t) = I_1(t) + I_2(t)$$
$$= (I_0(t) + I_0(t-T))/2.$$

Fourier transform of the above expressions provides the following frequency spectra $f_0(\nu)$, $f_1(\nu)$, $f2(\nu)$ and $f_{12}(\nu)$ of intensity changes of the source pulse train ($L_0$), the two light pulses ($L_1$ and $L_2$) and the second light pulse train ($L_{12}$) where FT represents the Fourier transform and $\nu$ represents frequency:

$$f_0(\nu) = FT(I_0(t))$$

$$f_1(\nu) = FT(I_1(t))$$
$$= FT(I_0(t)/2)$$
$$= f_0(\nu)/2$$

$$f_2(\nu) = FT(I_2(t))$$
$$= FT(I_0(t-T)/2)$$
$$= f_0(\nu) \cdot \exp(-2\pi i T\nu)/2$$

$$f_{12}(\nu) = FT(I_{l12}(t))$$
$$= FT(I_1(t)) + I_2(t))$$
$$= f_0(\nu) \cdot (1 + \exp(-2\pi i T\nu))/2$$
$$= \exp(-\pi i T\nu) \cdot f_0(\nu) \cdot (\exp(\pi i T\nu) + \exp(-\pi i T\nu))/2$$
$$= \exp(-\pi i T\nu) \cdot f_0(\nu) \cdot \cos(\pi T\nu).$$

Figure 5:
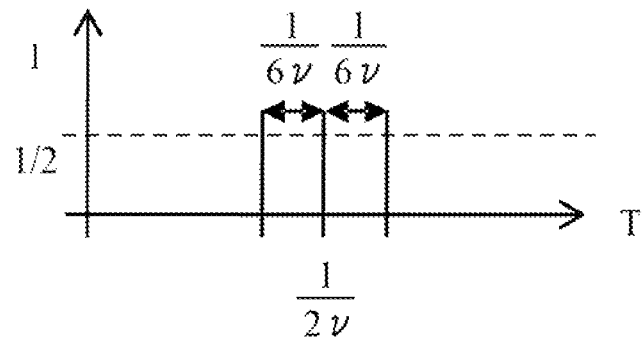
FIG. 5 shows a range of a delay time T in Embodiment 1.

A ratio of absolute values of the frequency spectra of the intensities $I_{12}$ and $I_0$ of the second light pulse train and the raw light pulse train is as follows and as shown in FIG. 5:

$$|f_{12}(\nu)|/|f_0(\nu)| = |\cos(\pi T\nu)|.$$

That is, setting the delay time T to $1/(2\nu)$ makes the value of $|f_{12}(\nu)|/|f_0(\nu)|$ zero, and the combined intensity $I_{12}(t)$ of the second light pulse train does not include a component of the frequency $\nu$.

Therefore, when the pulse interval of the first light pulse train (Stokes light) is represented by $\tau_S$, its repetition frequency $\nu_S$ (first repetition frequency) is as follows:

$$\nu_S = 1/\tau_S.$$

Thus, setting the delay time T to $1/(2\nu_S)(=\tau_S/2)$ makes it possible to remove the component of the frequency $\nu_S$ from the second light pulse train.

Moreover, even if the delay time T does not coincide with $\tau_S/2$, satisfying the condition of the expression (1) ($\tau_S/2-\tau_S/6 \leq T \leq \tau_S/2+\tau_S/6$) provides the following result:

$$|\cos(\pi T\nu_S)| \leq \frac{1}{2}.$$

In other words, satisfying the condition of the expression (1) can reduce the component of the frequency $\nu_S$ included in the intensity $I_{12}(t)$ of the second light pulse train to half or less of that included in the intensity $I_0(t)$ of the raw light pulse train.

As described above, when the delay time T in the delaying and combining part 30 is $\tau_S/2$ and when the delay time T is any time shifting (or intentionally shifted as in Embodiment 3 described later) therefrom within the range between $-\tau_S/6$ and $+\tau_S/6$, this embodiment enables generation of the second light pulse train in which the intensity noise component due to the light source is sufficiently reduced. Focusing of such a second light pulse train onto the sample 6 can improve the S/N ratio in the lock-in amplifier 12 to obtain a good molecular vibration image.

Example 2

Figure 6:
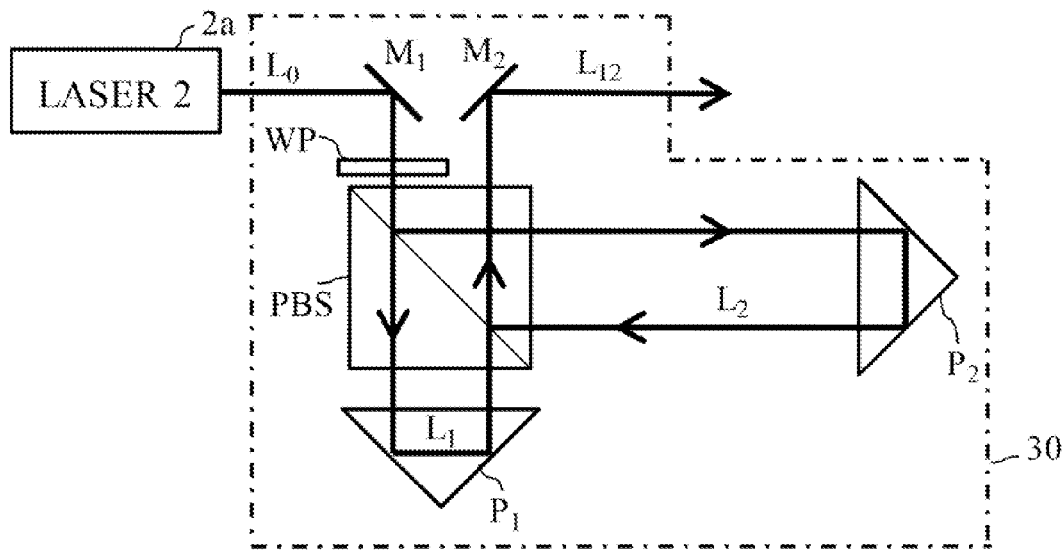
FIG. 6 is a block diagram showing a configuration of a delaying and combining part in an SRS detection apparatus of Embodiment 2 of the present invention.

FIG. 6 shows a detailed configuration of a delaying and combining part 30 in an SRS detection apparatus that is a second embodiment (Embodiment 2) of the present invention.

A raw light pulse $L_0$ emitted from a second light source 2a is reflected by a first mirror $M_1$ provided in the delaying and combining part 30 and then transmitted through a half wave plate WP to enter a polarization beam splitter PBS. The polarization beam splitter PBS reflects an S-polarized light pulse $L_2$ that is one light pulse of the entering raw light pulse $L_0$ and transmits the a P-polarized light pulse $L_1$ that is the other light pulse of the raw light pulse $L_0$. Thereby, the raw light pulse $L_0$ is divided into the P- and S-polarized light pulses $L_1$ and $L_2$ that are two light pulses. Adjusting an azimuth of an optic axis of the half wave plate WP makes it possible to equalize intensities of the P- and S-polarized light pulses $L_1$ and $L_2$ to each other.

The S-polarized light pulse $L_2$ reflected by the polarization beam splitter PBS proceeds to a delaying optical path (delayer) including a prism $P_2$. On the other hand, the P-polarized light pulse $L_1$ transmitted through the polarization beam splitter PBS enters the polarization beam splitter PBS again via a reflecting optical path including a prism $P_1$. The polarization beam splitter PBS serves as not only a divider but also a combiner.

The delaying optical path where the S-polarized light pulse $L_2$ passes is an optical path starting from the polarization beam splitter PBS, via the prism $P_2$, and returning to the polarization beam splitter PBS again. An optical path length of this delaying optical path has an optical path length difference $\Delta L$ from the reflecting optical path where the P-polarized light pulse $L_1$ passes, the reflecting optical path being an optical path starting from the polarization beam splitter PBS, via the prism $P_1$, and returning to the polarization beam splitter PBS again. The optical path length difference ΔL is set so as to delay the S-polarized light pulse $L_2$ with respect to the P-polarized light pulse $L_1$ by a delay time T within the range shown by the expression (1) described in Embodiment 1. The delay time T may be $\tau_S/2$ or any time shifting therefrom within the range between $-\tau_S/6$ and $+\tau_S/6$. The optical path length difference ΔL is set, by adjustment of positions of the prisms $P_1$ and $P_2$, so as to have the relationship shown by the expression (2) with the first pulse period $\tau_S$ and the light speed c.

The P-polarized light pulse $L_1$ returning from the reflecting optical path to the polarization beam splitter PBS is transmitted therethrough and the S-polarized light pulse $L_2$ returning from the delaying optical path to the polarization beam splitter PBS is reflected thereby, and thus the P- and S-polarized light pulses $L_1$ and $L_2$ are combined with each other. This combination of the P- and S-polarized light pulses $L_1$ and $L_2$ generates a second light pulse $L_{12}$ having combined intensity corresponding to a sum of the intensity of the P-polarized light pulse $L_1$ divided from the raw light pulse $L_0$ and the intensity of the S-polarized light pulse $L_2$ divided from a previous raw light pulse $L_0$ and delayed by the delay time T. The second light pulse $L_{12}$ thus generated proceeds from the delaying and combining part 30 toward the mirror 3 shown in FIG. 1.

The division of the raw light pulse $L_0$, the delay of the S-polarized light pulse $L_2$, the combination of the P- and S-polarized light pulses $L_1$ and $L_2$ and the constant combined intensity of the combined second light pulse train are similar to those described in Embodiment 1 with reference to FIGS. 3A to 3D.

This embodiment also enables generation of the second light pulse train in which the intensity noise component is sufficiently reduced, thereby enabling improvement of the S/N ratio in the lock-in amplifier 12 to obtain a good molecular vibration image.

This embodiment divides the raw light pulse into two light pulses whose polarization directions are mutually different (orthogonal) and then combines them. Therefore, even if the delay time T is set to, for example, $\tau_S/2$, this embodiment can combine the two light pulses without interference therebetween, which makes it possible to generate the second light pulse train without generating noise due to the interference.

Example 3

Figure 7:
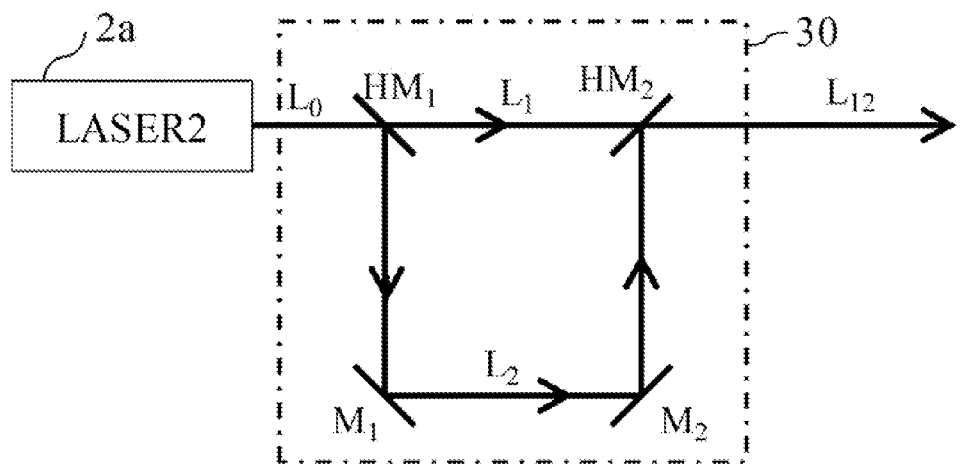
FIG. 7 is a block diagram showing a configuration of a delaying and combining part in an SRS detection apparatus of Embodiment 3 of the present invention.

FIG. 7 shows a detailed configuration of a delaying and combining part 30 in an SRS detection apparatus that is a third embodiment (Embodiment 3) of the present invention. This embodiment is a modified example, and constituent elements of the delaying and combining part 30 are same as those in Embodiment 1.

Although description was made of a possibility of the interference between the two light pulses to be combined when the delay time T is set to $\tau_S/2$ in Embodiment 2, this embodiment will describe a method to avoid that possibility without using polarized light as Embodiment 2. Specifically, this embodiment sets the delay time T within the range shown by the expression (1) in Embodiment 1 and within a range shown by the following expression (3) where p represents a pulse width of the second light pulse:

$$|T-(\tau_S/2)| \geq 2p \qquad (3)$$

On the basis of the expression (3), an optical path length difference ΔL of the delaying optical path where the light pulse $L_2$ passes from the optical path where the light pulse $L_1$ passes is set so as to have not only the relationship shown by the expression (2) in Embodiment 1, but also a relationship shown by the following expression (4) with $\tau_S$, c and p:

$$|\Delta L - c\tau_S/2| \geq 2cp \qquad (4)$$

Figure 8:
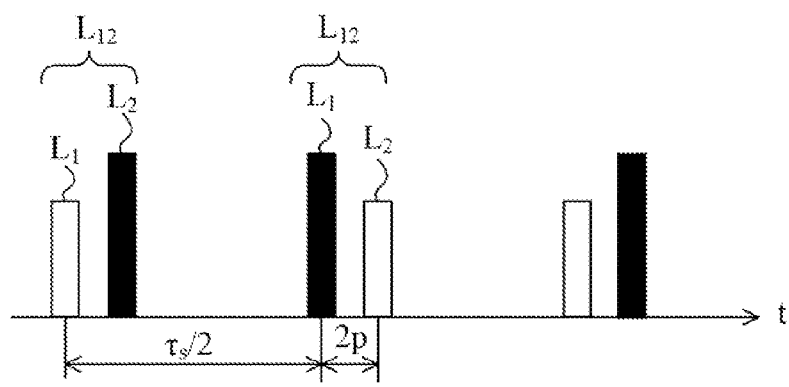
FIG. 8 shows light pulse trains generated by the delaying and combining part in Embodiment 3.

Setting the delay time T within the range of the expression (3) or setting the optical path length difference ΔL within the range of the expression (4) avoids direct overlap of the light pulses $L_1$ and $L_2$ to be combined with each other, as shown in FIG. 8. Therefore, such setting can prevent the interference between the light pulses $L_1$ and $L_2$ due to their combination, which can avoid generation of noise caused by the interference.

Since the lock-in amplifier 12 can detect combined intensity of the light pulses $L_1$ and $L_2$ even when the light pulses $L_1$ and $L_2$ do not overlap each other, non-overlap thereof does not influence detection sensitivity of the lock-in amplifier 12. This is because a desirable pulse width of the second light pulse is a width from a few picoseconds to tens of picoseconds, which is sufficiently shorter than the delay time T.

Embodiment 4

Figure 9:
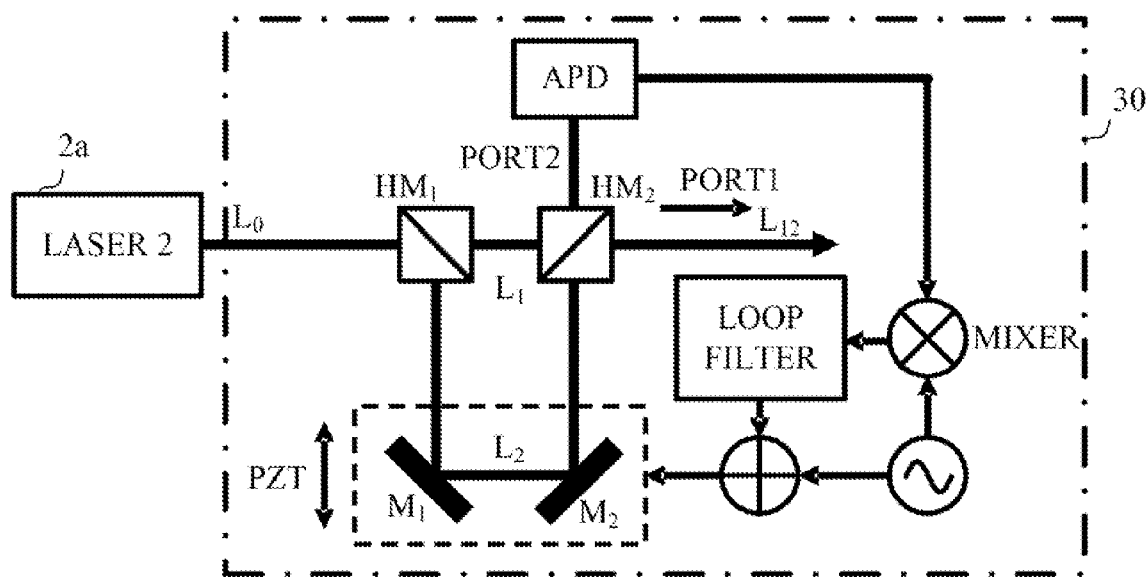
FIG. 9 is a block diagram showing a configuration of a delaying and combining part in an SRS detection apparatus of Embodiment 4 of the present invention.

FIG. 9 shows a detailed configuration of a delaying and combining part 30 in an SRS detection apparatus that is a fourth embodiment (Embodiment 4) of the present invention. This embodiment is another modified example of Embodiment 1 that suppresses generation of noise due to interference between two light pulses to be combined with each other, which is different from Embodiment 3.

This embodiment can suppress the generation of the noise even if the setting of the delay time T to $\tau_S/2$ in the delaying and combining part 30 causes the interference between the two light pulses to be combined with each other.

The raw light pulse $L_0$ emitted from the second light source 2a enters a first half mirror $HM_1$ provided in the delaying and combining part 30 to be divided into two light pulses $L_1$ and $L_2$. Of these light pulses $L_1$ and $L_2$, one light pulse $L_2$ proceeds to a delaying optical path including mirrors $M_1$ and $M_2$, and the other light pulse $L_1$ proceeds directly to a second half mirror $HM_2$.

Each of the mirrors $M_1$ and $M_2$ is configured to be movable in a direction where an optical path length difference ΔL of the delaying optical path from an optical path of the light pulse $L_1$ is changed, by an electrostrictive effect of a piezoelectric element PZT. The piezoelectric element PZT is driven at its resonance frequency (for example, about 10 kHz).

The light pulse $L_2$ that has passed through the delaying optical path is combined with the light pulse $L_1$ at a second half mirror $HM_2$.

This embodiment provides an interferometer using, as one output port (Port 2), the second half mirror $HM_2$ combining the two light pulses $L_1$ and $L_2$ with each other. This embodiment receives output light from the output port (Port 2) with an avalanche photodiode APD and phase-detects a photocurrent in the avalanche photodiode APD, which enables calculation of a shift amount of the optical path length of the delaying optical path from its optimal length. Then, this embodiment feeds back the shift amount to the piezoelectric element PZT to always provide minute optical path length modulation such that the optical path length of the delaying optical path, that is, the optical path length difference ΔL may cause the two light pulses $L_1$ and $L_2$ to always overlap each other with a same phase difference (that is, such that the output of the output port (Port 2) is minimized).

A second light pulse $L_{12}$ generated by the combination of the two light pulses $L_1$ and $L_2$ by the second half mirror $HM_2$ proceeds from another output port (Port 1) of the interferometer toward the mirror 3 shown in FIG. 1.

Thus, in this embodiment, since the two light pulses $L_1$ and $L_2$ always overlap each other with the same phase difference, the noise is not generated even if the two light pulses $L_1$ and $L_2$ interfere with each other. Therefore, this embodiment can generate the second light pulse train without generating the noise due to the interference.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-048110, filed on Mar. 4, 2011, which is hereby incorporated by reference herein in its entirety.

INDUSTRIAL APPLICABILITY

The present invention provides a stimulated Raman scattering detection apparatus having a good S/N ratio and being applicable to microscopes, endoscopes and the like.

The invention claimed is:

1. A stimulated Raman scattering detection apparatus comprising:
   a first light pulse generator configured to generate first light pulses with a first pulse period;
   a second light pulse generator configured to generate second light pulses with a second pulse period shorter than the first pulse period, the second light pulse having a light frequency different from that of the first light pulse,
   an optical system configured to combine the first and second light pulses and configured to focus the combined first and second light pulses onto a sample; and
   a detector configured to detect the second light pulses intensity-modulated by stimulated Raman scattering generated by focusing of the combined first and second light pulses onto the sample,
   wherein the second light pulse generator includes:
   a divider configured to divide each of raw light pulses into two light pulses, the raw light pulses being emitted from a light source with the second pulse period;
   a delayer configured to delay one light pulse of the two light pulses with respect to the other light pulse thereof by a delay time T; and
   a combiner configured to combine the divided two light pulses to generate the second light pulses, and
   wherein the delay time T is included within the following range:

$\tau_S/2-\tau_S/6 \leq T \leq \tau_S/2+\tau_S/6$, where $\tau_S$ represents the first pulse period.

2. The stimulated Raman scattering detection apparatus according to claim 1,
   wherein the delayer is configured to provide, to an optical path where the one light pulse passes, an optical path length difference $\Delta L$ from that where the other light pulse passes, and
   wherein the optical path length difference $\Delta L$, the first pulse period $\tau_S$ and a light speed c have the following relationship:

$|\Delta L - c\tau_S/2| \leq c\tau_S/6$.

3. The stimulated Raman scattering detection apparatus according to claim 1,
   wherein the delay time T is included within the following range:

$|T-(\tau_S/2)| \geq 2p$ where p represents a pulse width of the second light pulse.

4. The stimulated Raman scattering detection apparatus according to claim 1,
   wherein the divider is configured to divide the raw light pulse from the light source into the two light pulses whose polarization directions are mutually different.

5. The stimulated Raman scattering detection apparatus according to claim 1,
   wherein the detector includes a lock-in amplifier configured to synchronously detect the second light pulse intensity-modulated by the stimulated Raman scattering with the first pulse period.

6. A stimulated Raman scattering detection method comprising:
   generating first light pulses with a first pulse period;
   generating second light pulses with a second pulse period shorter than the first pulse period, the second light pulse having a light frequency different from that of the first light pulse;
   focusing the first and second light pulses onto a sample; and
   detecting the second light pulses intensity-modulated by stimulated Raman scattering generated by focusing of the first and second light pulses onto the sample,
   wherein the method further comprising for generating the second light pulses:
   dividing each of raw light pulses into two light pulses, the raw light pulses being emitted from a light source with the second pulse period;
   delaying one light pulse of the two light pulses with respect to the other light pulse thereof by a delay time T; and
   combining the divided two light pulses to generate the second light pulses, and
   wherein the delay time T is included within the following range:

$\tau_S/2-\tau_S/6 \leq T \leq \tau_S/2+\tau_S/6$, where $\tau_S$ represents the first pulse period.

* * * * *